United States Patent [19]

McFadden et al.

[11] Patent Number: 5,834,419
[45] Date of Patent: Nov. 10, 1998

[54] CHEMOKINE BINDING PROTEIN AND METHODS OF USE THEREFOR

[75] Inventors: Grant McFadden; Alexandra Lucas, both of Edmonton, Canada

[73] Assignee: The John P. Robarts Institute, London, Canada

[21] Appl. No.: 634,924

[22] Filed: Apr. 19, 1996

Related U.S. Application Data

[63] Continuation-in-part of Ser. No. 424,850, Apr. 19, 1995, abandoned.

[51] Int. Cl.$^6$ .......................... C61K 38/16; C07K 14/065
[52] U.S. Cl. ..................................... 514/2; 514/8; 514/12; 530/350; 424/84
[58] Field of Search ................................ 530/350; 514/2, 514/8, 12; 424/84

[56] References Cited

U.S. PATENT DOCUMENTS 5,464,938  11/1995  Smith et al. ............................. 530/350

FOREIGN PATENT DOCUMENTS

WO 91/16431  10/1991  WIPO .

OTHER PUBLICATIONS

Mossman et al., "Myxoma Virus M–T7, a Secreted Homolog of the Interferon–y Receptor, Is a Critical Virulence Factor for the Development of Hyxomatosis in European Rabbits", *Virology,* vol. 215, pp. 17–30, 1996.

McFadden et al., "Interruption of Cytokine Networks by Poxviruses: Lessons from Myxoma Virus", *Journal of Leukocyte Biology,* vol. 57, pp. 731–738, 1995.

Upton et al., "Encoding of a Homolog of the IFN–y Receptor by Myxoma Virus", *Science,* Nov. 20, 1992, vol. 258, pp. 1369–1372.

Mossman et al., "The Myxoma Virus–solube Interferon–y Receptor Homolog, M–T7, Inhibits Interferon–y in a Species–specific Manner", *The Journal of Biological Chemistry,* vol. 270, No.7, Issue of Feb. 17, pp. 3031, 3038, 1995.

Mossman et al., "Species Specificity of Ectromelia Virus and Vaccinia Virus Interferon–y Binding Proteins", *Virology,* vol. 208, pp. 762–769, 1995.

Neote et al 1993 (Cell 72, 415).

Chaudhuri et al 1994 (J. Biol. Chem. 269, 7835).

Ahuja et al. 1994 (Immunol. Today 15, 281).

Horuk et al 1994 (Trends Pharm. Sci. 15, 159).

*Primary Examiner*—Stephen Walsh
*Assistant Examiner*—Daryl A. Basham
*Attorney, Agent, or Firm*—Fish & Richardson, P.C.

[57] ABSTRACT

The present invention provides a method of use for a novel type I chemokine binding protein encoded by poxviruses and having amino acid sequence homology with the myxoma virus T7 interferon-γ receptor homolog against disease syndromes associated with acute or chronic dysregulated inflammatory responses.

6 Claims, 14 Drawing Sheets

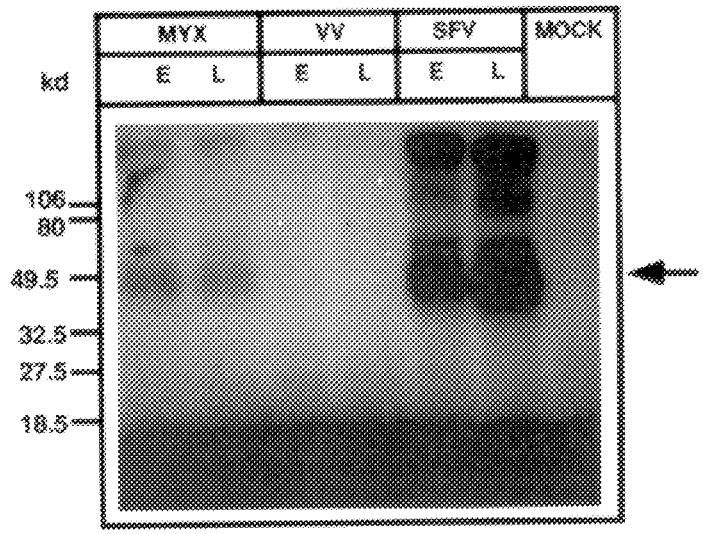
FIG. IA-1
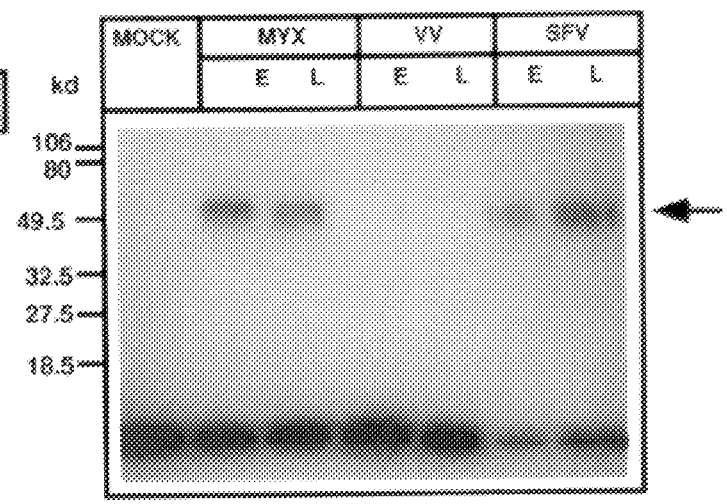
FIG. IA-2
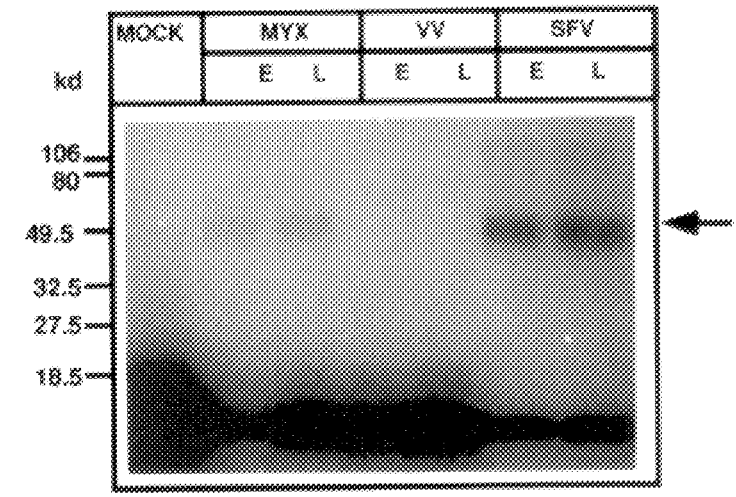
FIG. IA-3

T-7 500pg      p=0.004
T-7 5000pg     p=0.0062
T-7 50000pg    p=0.0189
TOTAL:         p=0.0001

▩ T-7

╱ COLUMN 3SALINE CONTROL GROUP

500pg      p=0.0127
5000pg     p=0.00187
50000pg    p=0.0443
TOTAL:      p=0.0003

▨ T-7

⧄ SALINE CONTROL GROUP

CHEMOKINE BINDING PROTEIN AND METHODS OF USE THEREFOR

This application is a continuation-in-part of U.S. Ser. No. 08/424,850, filed Apr. 19, 1995, now abandoned.

BACKGROUND OF THE INVENTION

1. Field of the Invention

This invention relates generally to the field of immunology and specifically to a chemokine binding protein encoded by a variety of poxviruses and methods of use therefor.

2. Description of Related Art

It is becoming increasingly clear that viruses which make their living within cells of higher-order vertebrates must have evolved to specifically avoid the host immune system (Gooding, L., Cell, 91:5–7, 1992; Marrack, P. and Kappler, J., Cell, 76:323–332, 1994; Smith, G., Trends in Micro., 82:80–88, 1994). In fact, virus survival is dependent upon strategies which can evade, suppress, counteract, or otherwise confound the myriad of host responses to a foreign invader. The selection pressure conferred by the effector arms of the immune system can clearly be a powerful element of evolutionary pressure, and all eukaryotic viruses existing today contain imprints or remnants of their battles with the immune system, either as encoded proteins or as evidenced by their particular biological survival strategies.

The larger DNA viruses (i.e. the adenoviruses, herpesviruses, iridoviruses and poxviruses) specifically encode proteins that function to protect the virus from immune recognition and/or clearance by the infected host. Such "subversive" viral proteins are now providing information concerning the functional operations of the immune system, and it is likely that many more discoveries of new members of this growing family will be identified in the future.

In the 1980's the term "virokine" was proposed to describe virus-encoded proteins secreted from infected cells which function by mimicking extracellular signaling molecules such as cytokines or other secreted regulators important for the host immune repertoire (Kotwal, G. and Moss, B., Nature, 335:176–178, 1988). Later, in the 1990's the term "viroceptor" was introduced to account for the observation that some virus encoded proteins that mimic important cellular receptors and function by diverting host cytokines away from their normal receptors, thus interrupting the immune circuitry at its earliest stages (Upton, et al., Virology, 184:370, 1991; Schreiber and McFadden, Virology, 204:692–705, 1994).

Recent studies on a particular poxvirus, myxoma virus, have shown that the virus disrupts the immune system by a variety of strategies (McFadden and Graham, Seminars in Virology, 5:421–429, 1994). Myxoma virus is the infectious agent of a virulent systemic disease of domestic rabbits called myxomatosis. Originally described in the last century, myxoma was the first virus pathogen discovered for a laboratory animal and was the first viral agent ever deliberately introduced into the environment for the explicit purpose of pest eradication. Since its release into the Australian and European feral rabbit populations more than 40 years ago, the field strains of both the rabbit and virus have been subjected to mutual evolutionary and selective pressures that have resulted in a steady-state enzootic in the inoculated areas (Fenner, F. and Ratcliffe, F. N., "Myxomatosis", Cambridge University Press, London, 1965).

Myxoma shares many of the biologic features associated with other poxviruses, namely cytoplasmic location of replication and a large double stranded DNA genome (160 kilobases). Multiple lines of evidence indicate that myxoma, like all poxviruses, encodes multiple gene products whose function is to permit the spread and propagation of the virus in a variety of host tissues. Some of these viral proteins specifically counteract or subvert the development of the host inflammatory response and acquired cellular immunity, and poxviruses in general have been a rich source of such immunomodulatory proteins (Turner, P. C., and Moyer, R. W., Cur. Top. Microbiol. Imm., 163:125–152, 1990; Buller, R. M. L., and Palumbo, G. J., Micro. Dev., 55:80–122, 1991; Smith, G. L., J, Gen. Virol., 94:1725–1740, 1993; McFadden, G., (Ed.), "Viroceptors, virokines and related immune modulators encoded by DNA viruses", R. G. Landes Co., Austin Tex., 1995).

Examples of such immunomodulatory gene products include myxoma growth factor (MGF), which stimulates neighboring cells in a paracrine-like fashion via the cellular epidermal growth factor receptor (Upton, et al., J. Virol., 61:1271–1275, 1987; Opgenorth, et al., Virol., 186:185–191, 1992; Opgenorth, et al., Virol., 192:701–708, 1992; Opgenorth, et al., J. Virol., 66:4720–4731, 1992); Serp 1, a secreted glycoprotein with serine protease inhibitor activity, that prevents development of the early inflammatory response (Upton, et al., Virol., 179:628–631, 1990; Lomas, et al., JBC, 268:516–521, 1993; Macen, et al., Virol., 195:348–363, 1993); T2, a secreted viral homologue of the cellular tumor necrosis factor (TNF) receptor superfamily, that binds and inhibits rabbit TNF (Smith, et al., BBRC, 176:335–342, 1991; Schreiber, M. and McFadden, G., supra, 1994; Upton, et al., supra, 1991); T7, a secreted viral homologue of the cellular interferon-γ receptor, that binds and inhibits rabbit interferon-γ (Upton, et al., Science, 258:1369, 1992; Upton and McFadden, Methods in Molecular Genetics, 4:383, 1994; Mossman, et al., In: "Viroceptors, virokines and related immune modulators" p. 41–54 Ed. McFadden, R. G. Landers, Co., 1995); and M11L, a surface receptor-like protein that interferes within the inflammatory response by an unknown mechanism (Opgenorth, et al., supra; Graham, et al., Virol, 191:112–124, 1992);

Immunomodulatory proteins also include chemotactic cytokines, called "chemokines". Chemokines are small molecular weight immune ligands which are chemoattractants for leukocytes, such as especially neutrophils, basophils, monocytes and T cells. There are two major classes of chemokines which both contain four conserved cysteine residues which form disulfide bonds in the tertiary structure of the proteins. The a class is designated C-X-C (where X is any amino acid), which includes IL-8, CTAP-III, gro/MGSA and ENA-78; and the β class, designated C-C, which includes MCP-1, MIP-1α and β, and regulated on activation, normal T expressed and secreted protein (RANTES). The designations of the classes are according to whether an intervening residue spaces the first two cysteines in the motif. In general, most C-X-C chemokines are chemoattractants for neutrophils but not monocytes, whereas C-C chemokines appear to attract monocytes but not neutrophils. Recently, a third group of chemokines, the "C" group, was designated by the discovery of a new protein called lymphotactin (Kelner, et al., Science, 266:1395–1933, 1994). The chemokine family is believed to be critically important in the inflammation of lymphocytes and monocytes into sites of inflammation.

It is highly likely that more immunomodulatory viral genes remain to be discovered. Not only will these and related gene products provide useful tools to dissect out the different arms of the host antiviral defense mechanisms, but they may also provide new probes to identify novel elements of the cellular immune repertoire and new classes of drugs to suppress inflammation and dysregulation of the immune system.

SUMMARY OF THE INVENTION

The present invention describes an unexpectedly discovered novel soluble virus-specific inhibitor for a class of cytokines which are involved in leukocyte chemotaxis and are collectively referred to as "chemokines". The protein of the invention is a Type I "chemokine binding protein" (CBP-I) (SEQ. ID NO:2)and is a gene product of the T7 gene of myxoma virus, which previously had been shown to encode the interferon-γ (IFN-γ) receptor homologue. However, in sharp contrast to the extreme specificity of the T7 gene product for the rabbit ligand (IFN-γ), the CBP-I of the invention binds very well to mouse and human chemokines. The CBP-I and related homologues encoded by other poxviruses is useful for treatment of a variety of inflammatory disorders in which excessive influx of leukocytes is associated with the pathogenic process.

BRIEF DESCRIPTION OF THE DRAWINGS

FIG. 1A shows an SDS-PAGE of $I^{125}$-labelled IL-8, RANTES and MIP-1β after exposure to poxviral-secreted proteins.

FIG. 3A shows myxoma, vaccinia, and SFV. FIG. 3B shows myxoma, cow pox, rabbit pox, ectromelia, and SFV.

DETAILED DESCRIPTION OF THE INVENTION

Figure 1B:
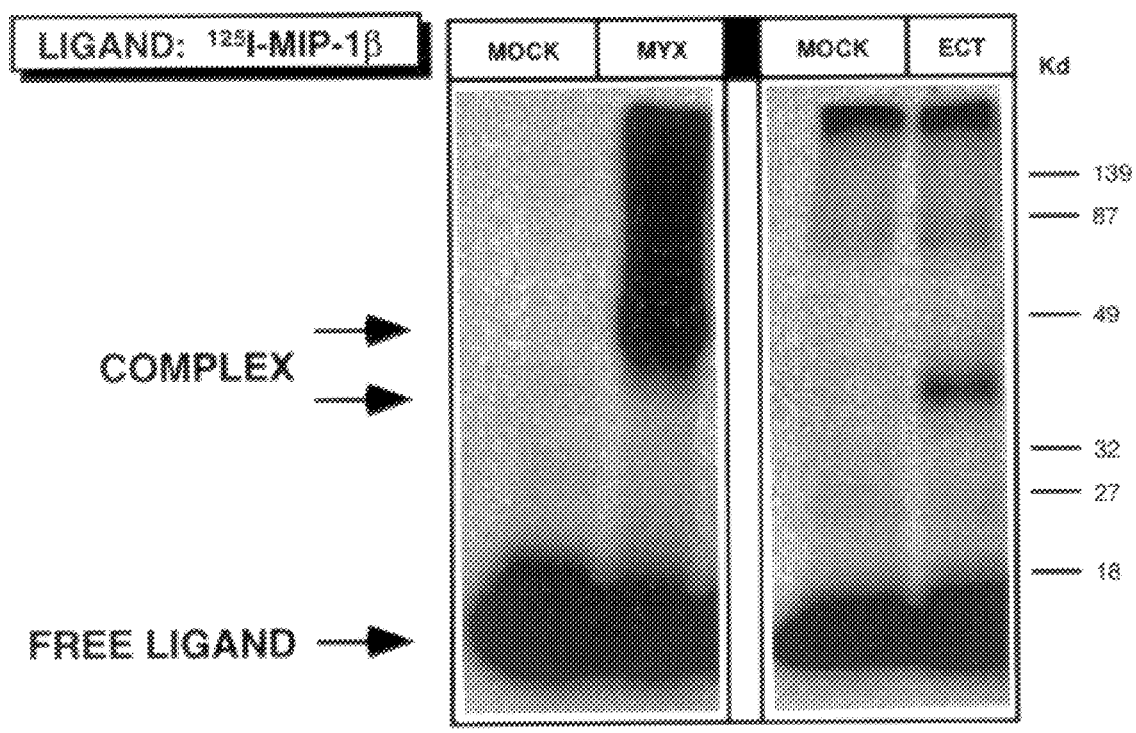
FIG. 1B shows an SDS-PAGE of $I^{125}$-MIP- 1β in myxoma or ectromelia virus-infected cells.
Figure 2A:
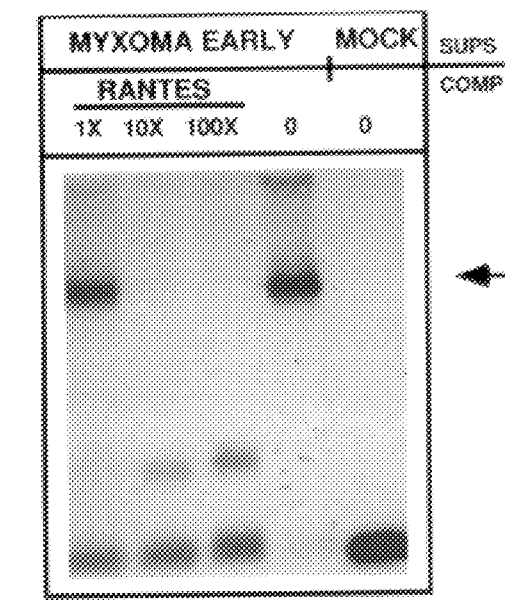
FIG. 2 shows an SDS-PAGE of $I^{125}$-labelled RANTES as a ligand for myxoma secreted proteins and competition with unlabelled RANTES, MIP- 1β, MIP-1γ, IL-8 and MCP-1.
Figure 2B:
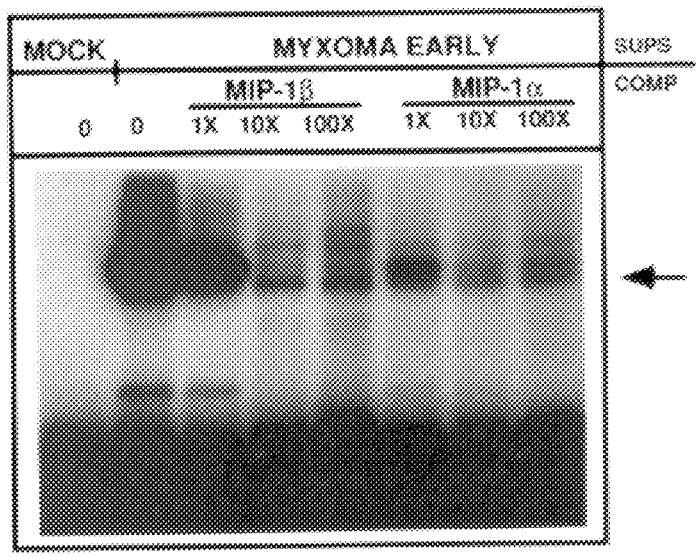
Figure 2C:
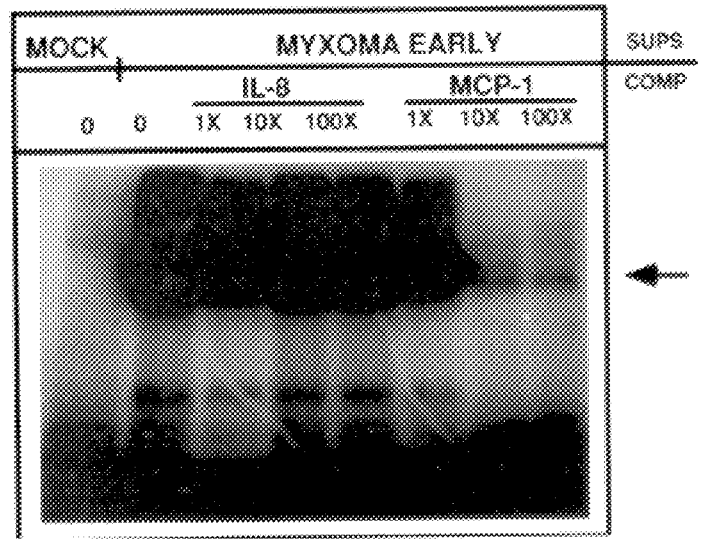
Figures 1, 3A:
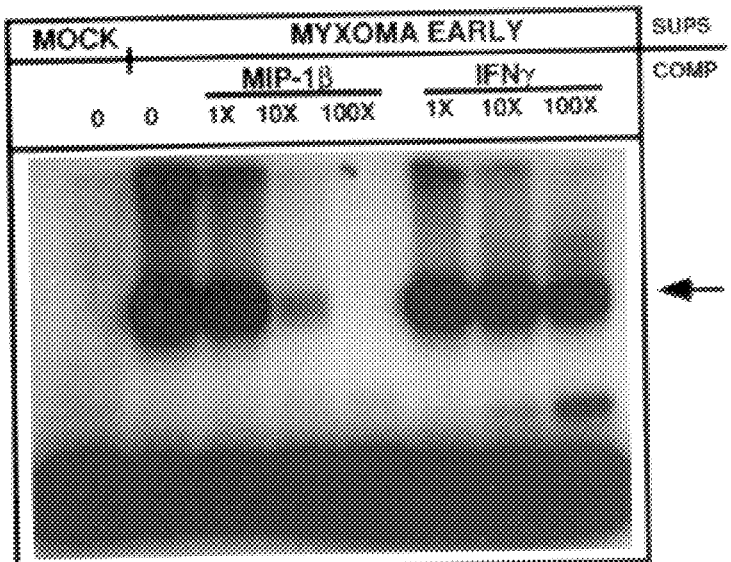
FIG. 3A and 3B shows an SDS-PAGE of $I^{125}$-labelled MIP-1β as a ligand for poxviral secreted proteins and competition with unlabelled MIP-1β, IFN-γ, MCAF, MIP-1α, RANTES and IL-8.
Figures 2, 3A:
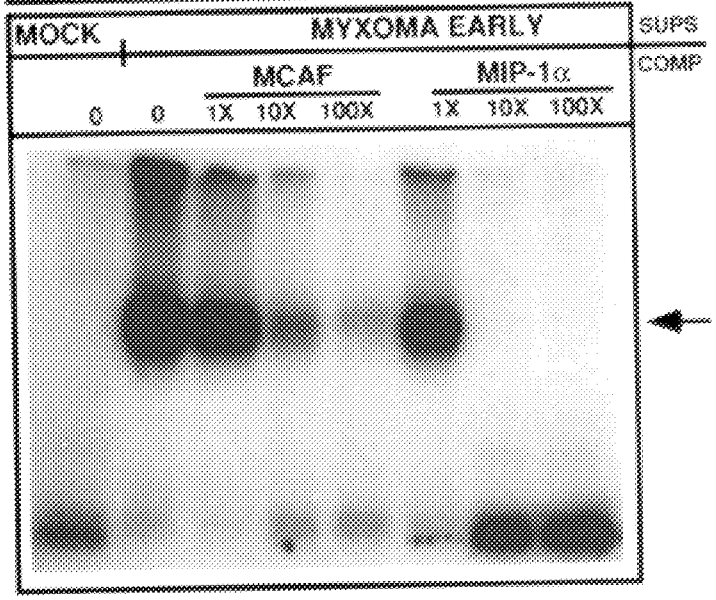
Figures 3, 3A:
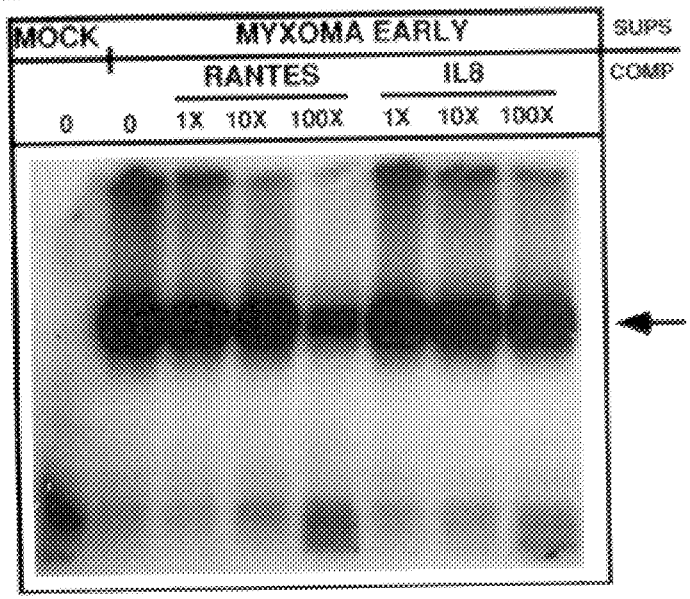
Figure 3B:
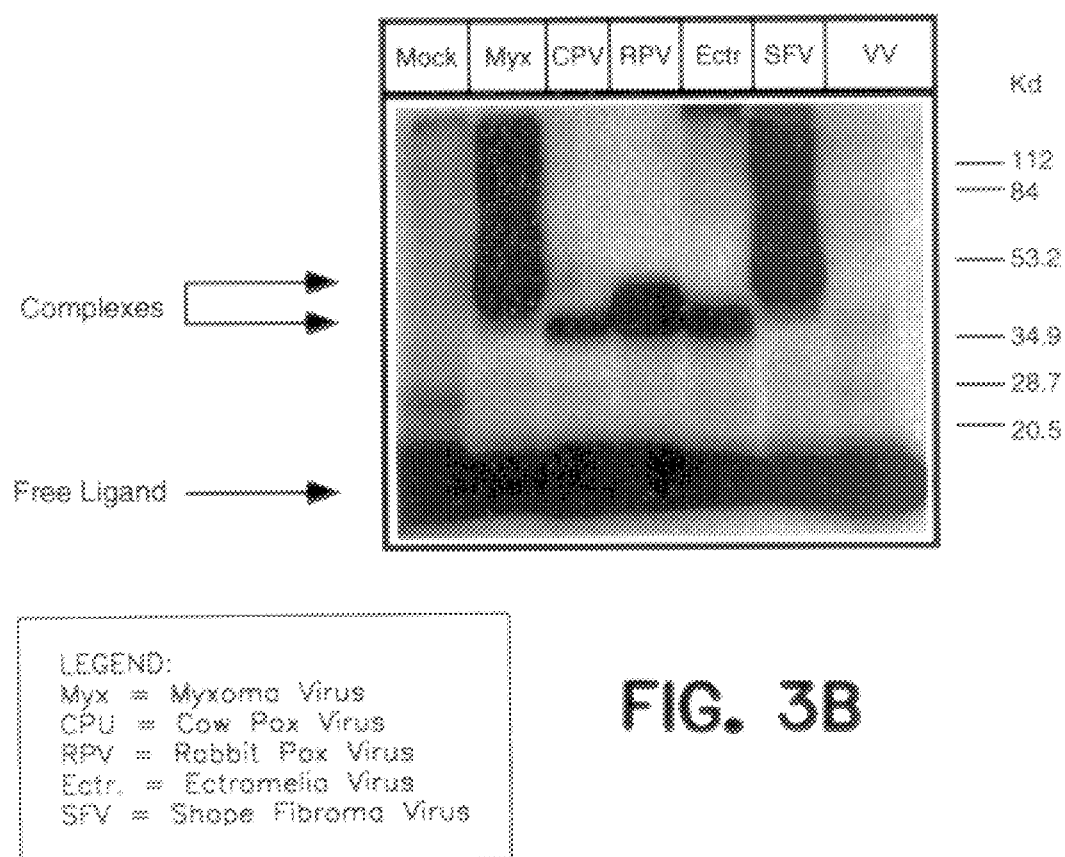
Figure 4A:
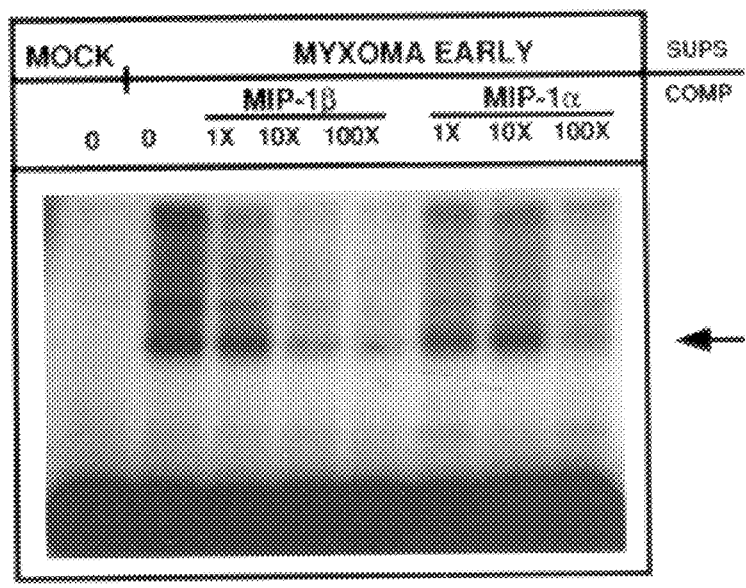
FIG. 4 shows an SDS-PAGE of $I^{125}$-labelled IL-8 as a ligand for myxoma secreted proteins and competition with unlabelled MIP-1β, IFN-γ, MCAF, and MIP-1α.
Figure 4B:
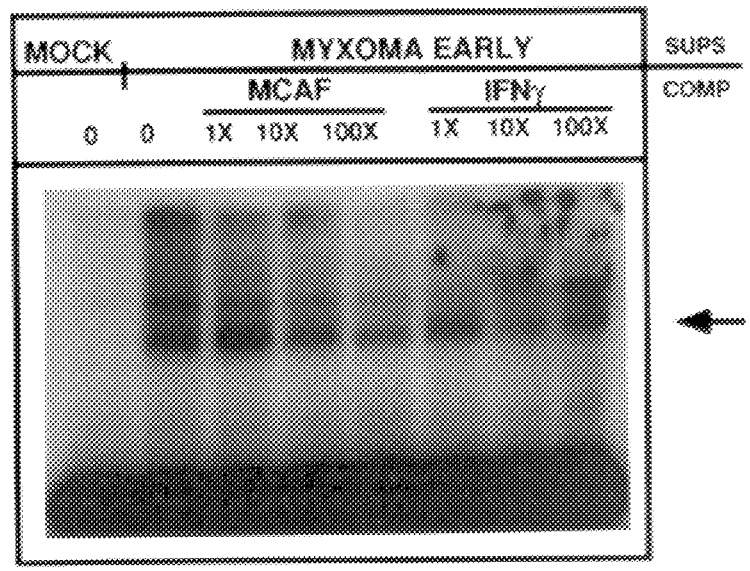
Figure 5:
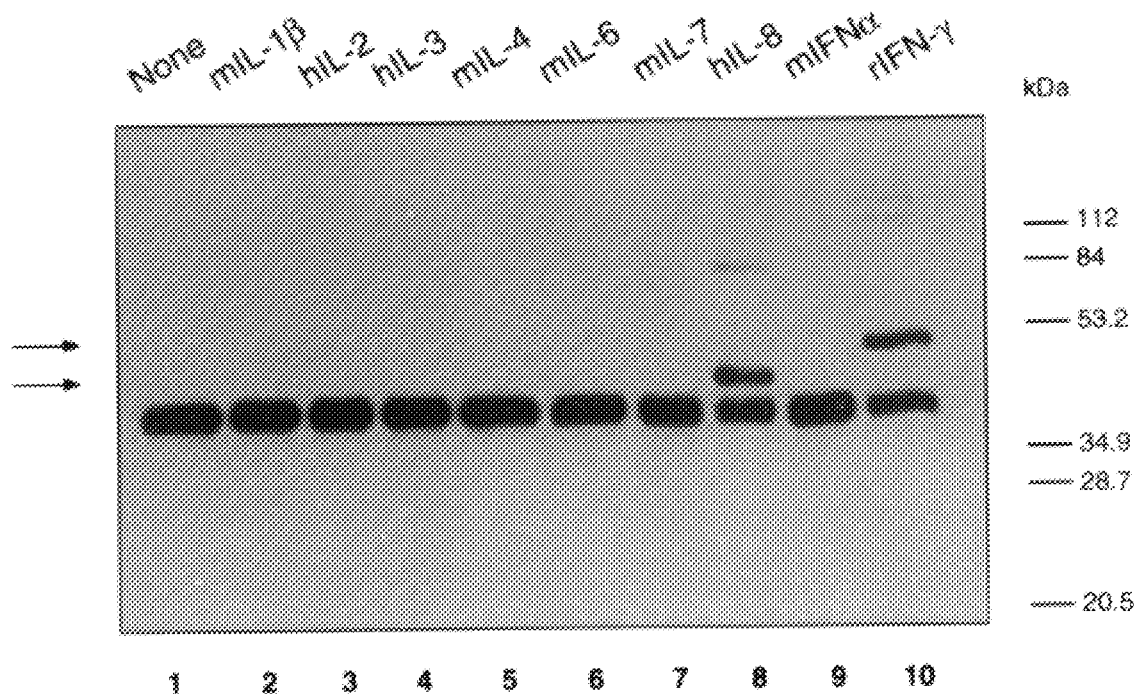
FIG. 5 shows a Western blot that displays T7 protein following interaction with a variety of cytokines (IL-1β, IL-2, IL-3, IL-4, IL-6, IL-7, IL-8, IFNα, and IFN-γ).
Figure 6:
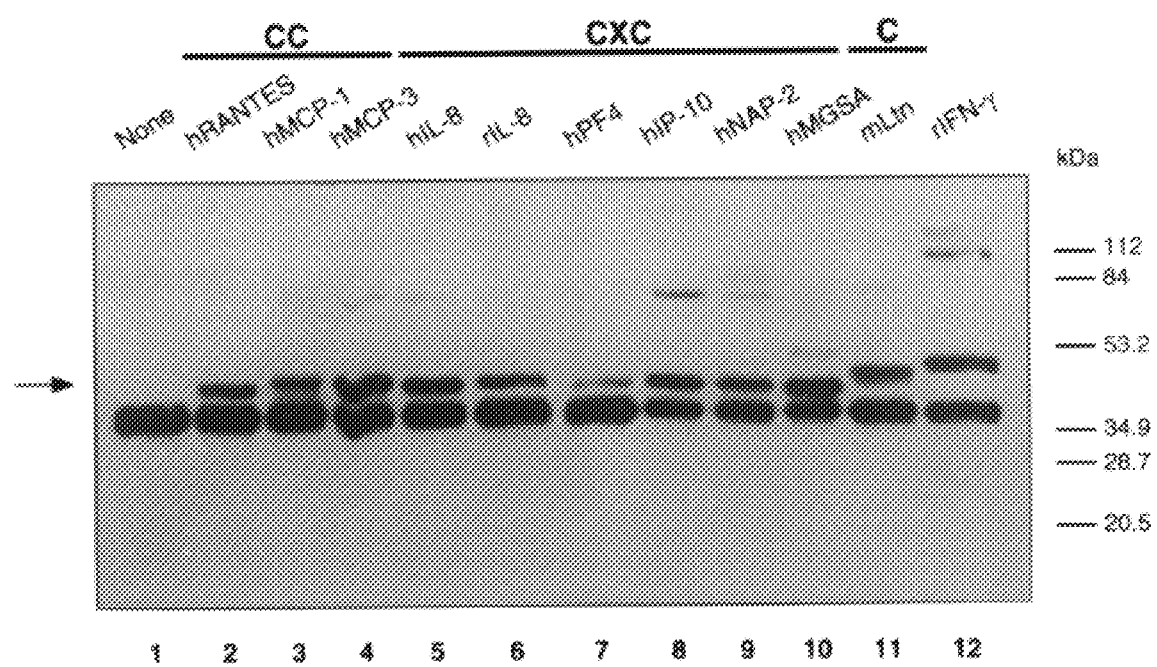
FIG. 6 shows a Western blot that displays T7 protein following interaction with a variety of chemokines (RANTES, MCP-1, MCP-3, IL-8, PF4, IP-10, NAP-2, MGSA and lymphotactin).

The findings of the present invention provide an important new source of anti-immune proteins which have the potential to treat a wide range of immunopathological conditions associated with the trafficking of lymphocytes and monocytes from the circulation to tissue sites during inflammation and immune responses to damage, infection and various disease states.

The exemplary Type I chemokine binding protein (CBP-I) of the invention is the major secreted protein from cells infected with myxoma virus and is encoded by the M-T7 open reading frame (Upton, et al., *Science,* 258:1369, 1992; and GenBank Accession No: M81919; SEQ ID NO: 1 and SEQ ID NO:2). This protein has significant sequence similarity to the human and mouse receptors for interferon gamma (IFN-γ). Further, the myxoma M-T7 protein specifically binds rabbit IFN-γ, but not mouse or human IFN-γ (Mossman, et al., *J Biol. Chem.,* 270:3031–3038, 1995).

The term "chemokine binding protein" refers to a protein which binds to and inhibits one or more chemokines. A "chemoline" is a class of cytokines which are responsible for leukocyte chemotaxis. The α class of chemokines is designated C-X-C (where X is any amino acid), which includes interleukin-8 (IL-8), connective tissue activating protein III (CTAP-III), melanocyte growth stimulatory activity (MGSA) gro/MGSA, IFN-γ inducible protein (IP-10), neutrophil activating peptide 2 (NAP2), β-thromboglobulin and epithelial-derived neutrophil attractant-78 (ENA-78); and the β class, designated C-C, which includes T-cell activation gene-3 (TCA-3), monocyte chemotactic proteins (MCP-1, 2, and 3), macrophage inflammatory proteins (MIP-1α and β), and regulated on activation, normal T expressed and secreted protein (RANTES).

Other chemokines can be detected by methods commonly used in the art. For example, a molecule may be tested using the Boyden chamber, which is the preferred microchemotaxis assay system for in vitro investigation of chemoattractant substances. A series of wells is formed into a plexiglass block, each well consisting of two chambers, upper and lower, which are separated by any one of several types of porous filters, such as nitrocellulose and polycarbonate, for example. The cell of interest, for example peripheral blood mononuclear cells (PBMC) are added to the top chamber of each well and the test substance, e.g., the chemoattractant, is added to the bottom chamber. If the cells in the top chamber are attracted to the substance in the bottom chamber, they will migrate along the theoretical concentration gradient which exists in solution and crawl through the pores of the filter and adhere to the bottom side of that filter.

Polypeptides suspected of being members of the chemokine family can now be screened using the CBP-I of the invention. Therefore, in one embodiment, the invention provides a method for screening and identifying novel chemokines comprising contacting free or matrix-bound CBP-I of the invention with a composition suspected of containing one or more chemokines and detecting binding of the CBP-I to the composition. Methods for detecting binding of the CBP-I to the composition (chemokine) will be known to those of skill in the art and include those described in the EXAMPLES herein.

If desirable, various labels can be used as means for detecting binding of CBP-I to a chemokine. Chemokines or the CBP-I can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels or will be able to ascertain such, using routine experimentation.

In another embodiment, the invention provides a method for treating an immunopathological disorder in a subject comprising administering to the subject a therapeutically effective amount of an anti-inflammatory protein characterized as having a molecular weight of approximately 30–40 kD, depending on the extent of glycosylation, as determined by reduced SDS-PAGE, having amino acid sequence homology with myxoma T7 interferon-γ receptor homolog, and having the biological function of myxoma T7 interferon-γ receptor homolog. The term "anti-inflamnatory" refers to reduction or suppression of an inflammatory response.

The glycosylated and secreted form of the exemplary CBP-I of the invention has an apparent molecular weight of approximately 38 kD as determined under reducing conditions on an SDS-PAGE. In addition, the protein has homology with the myxoma T7 IFN-γ receptor homolog. The term "homology" refers to the extent of identity between the CBP-I and the viral IFN-γ receptor at the amino acid level. Preferably, the CBP-I (SEQ. ID NO:2) has between 50–95% amino acid sequence homology with the myxoma T7 IFN-γ receptor. The homology requirement is not stringent, however, the CBP-I must retain the biological function of the myxoma T7 IFN-γ receptor. In other words, the homology is sufficient as long as the CBP-I binds and inhibits chemokines.

The invention includes a functional polypeptide, CBP-I, and functional fragments thereof As used herein, the term "functional polypeptide" refers to a polypeptide which possesses a biological function or activity which is identified through a defined functional assay and which is associated with a particular biologic, morphologic, or phenotypic response. Functional fragments of the CBP-I polypeptide, include fragments of CBP-I as long as the activity of CBP-I remains (e.g., binding to chemokines). Smaller peptides containing the biological activity of CBP-1 are included in the invention. Such peptides can be assayed for binding to chemokines by methods commonly known to those of skill in the art, including methods described in the EXAMPLES herein. The biological function can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the CBP-I primary amino acid sequence may result in proteins which have substantially equivalent activity as compared to the CBP-I polypeptide described herein. Such modifications may be deliberate, as by site-directed mutagenesis, or may be spontaneous. All of the polypeptides produced by these modifications are included herein as long as the activity of CBP-I is retained. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for CBP-I activity.

The CBP-I polypeptide of the invention also includes conservative variations of the polypeptide sequence. The term "conservative variation" as used herein denotes the replacement of an amino acid residue by another, biologically similar residue.

Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Examples of viral sources of the CBP-I used in the method of the present invention include myxoma virus, cowpox, shope fibroma virus, ectromelia, rabbitpox and other mammalian pox viruses, as long as the CBP-I has the biological function of an anti-inflammatory protein characterized as having a molecular weight of approximately 30–40 kD, depending on extent of glycosylation having homology with myxoma T7 interferon-γ receptor homolog, and having the biological function of myxoma T7 interferon-γ receptor homolog.

An immunopathological disorder treated by the method of the invention may be associated with production of chemokines and resultant accumulation of reactive leukocytes at afflicted tissues. The method comprises administering to the subject a therapeutically effective amount of CBP-I. The term "immunopathological disorder" refers to any disease which involves the immune response or immunity in general. "Therapeutically effective" as used herein, refers to that amount of CBP-I that is of sufficient quantity to ameliorate the cause of the immunopathological disorder. "Ameliorate" refers to a lessening of the detrimental effect of the disorder in the patient receiving the therapy. The subject of the invention is preferably a human, however, it can be envisioned that any animal with an immunopathological disorder can be treated by the method of the invention, for example, a SCID mouse grafted with human bone marrow (humanized SCID). Examples of immunopathological disorders which can be treated by the method of the invention include acquired immunodeficiency disorder (AIDS), toxic shock syndrome, allograft rejection, artherosclerotic plaque growth, ultraviolet and radiation responses, and disorders associated with the activation of T cells, B cells, macrophages, and other inflammatory leukocytes during the immune response and the acute phase response and disorders associated with advanced cancer such as tumor necrosis factor-mediated cachexia.

The invention provides a method of treating or ameliorating an immunopathological disorder including endotoxemia or septic shock (sepsis), or one or more of the symptoms of sepsis comprising administering to a subject displaying symptoms of sepsis or at risk for developing sepsis, a therapeutically effective amount of CBP-I. The term "ameliorate" refers to a decrease or lessening of the symptoms of the disorder being treated.

A patient who exhibits the symptoms of an immunopathological disorder may be treated with an antibiotic or antiviral agent in addition to the treatment with CBP-I. Typical antibiotics include an aminoglycoside, such as gentamycin or a beta-lactam such as penicillin, or cephalosporin. Therefore, a therapeutic method of the invention includes administering a therapeutically effective amount of CBP-I substantially simultaneously with administration of a bactericidal amount of an antibiotic or sufficient amount of an anti-viral compound.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated. Preferably, administration of CBP-I occurs within about 48 hours and preferably within about 2–8 hours, and most preferably, substantially concurrently with administration of the antibiotic.

Administration of a CBP-I in the method of the invention may also be used for ameliorating post-reperfusion injury. When treating arterial thrombosis, induction of reperfusion by clot lysing agents such as tissue plasminogen activator (t-PA) is often associated with tissue damage. Such tissue damage is thought to be mediated at least in part by leukocytes including but not limited to polymorphonuclear leukocytes (PMN). Therefore administration of the CBP-I would block leukocyte or PMN-endothelial interactions, and thereby diminish or prevent post-reperfusion injury. Administration of CBP-I is also useful for prevention of new onset and recurrent atherosclerotic plaque growth after arterial injury. Restenosis and new growth of plaque is believed to be exacerbated by the local inflammatory response to the internal layer of the artery wall.

The method of the invention is also useful for treatment of inflammation due to allergic or autoimmune disorders. Examples of allergic disorders include allergic rhinitis, asthma, atopic dermatitis, and food allergies. Examples of autoimmune disorders, where the immune system attacks the host's own tissues, include, but are not limited to, type 1 insulin-dependent diabetes mellitus, inflammatory bowel disease, dermatitis, meningitis, thrombotic thrombocytopenic purpura, Sjogren's syndrome, encephalitis, uveitis, leukocyte adhesion deficiency, rheumatoid and other forms of immune arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune hemolytic anemia, Hashirnoto's thyroiditis, Graves disease, habitual spontaneous abortions, Reynard's syndrome, glomerulonephritis, derrnatomyositis, chronic active hepatitis, celiac disease, autoimmune complications of AIDS, atrophic gastritis, ankylosing spondylitis and Addison's disease.

The method is also useful in treating non-malignant or immunological-related cell-proliferative diseases such as psoriasis, pemphigus vulgaris, Behcet's syndrome, acute respiratory distress syndrome (ARDS), ischemic heart disease, atherosclerosis, post-dialysis syndrome, leukemia, acquired immune deficiency syndrome, septic shock and other types of acute inflammation, and lipid histiocytosis. Essentially, any disorder which is etiologically linked to the pro-inflammatory process and cellular infiltration due to chemokine production (e.g., induction of IL-8, MIP-1α or β expression) would be considered susceptible to treatment.

The method of the invention is also useful for the treatment of microbial infections. Many microbes, such as bacteria, rickettsia, various parasites, and viruses, bind to vascular endothelium and leukocytes, and induce an inflammatory reaction resulting in production of interleukins for example. Thus, the CBP-I used in the method of the invention may be administered to a patient to prevent inflammation associated with such infections.

The dosage ranges for the administration of the CBP-I of the invention are those large enough to produce the desired effect in which the symptoms of the immune response show some degree of suppression. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 10 pg to 100 µg per dosage, in one or more dose administrations daily, for one or several days.

The CBP-I is administered by any suitable means, including parenteral, subcutaneous, intrapulmonary, intraareterial, intrarectal, intramuscular, and intranasal administration. Parenteral infusions include intramuscular, intravenous, intraarterial, or intraperitoneal administration. CBP-I may also be administered transdermally in the form of a slow-release subcutaneous implant for example, or orally in the form of capsules, powders or granules. CBP-I can also be administered by inhalation. For example, when used therapeutically for treatment of an inflammatory disorder of the lungs, a preferred route of administration would be by a pulmonary aerosol.

Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient is often mixed with excipients which are pharmaceutically acceptable and compatible with the active ingredient. Suitable excipients include water, saline, dextrose, glycerol and ethanol, or combinations thereof Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The invention also relates to a method for preparing a medicament or pharmaceutical composition comprising the CBP-I of the invention, the medicament being used for therapy of an undesirable immune response/inflammatory reaction wherein the immune response results in production of chemokines which bind to the CBP-I of the present invention.

The invention provides a pharmaceutical composition comprising at least one dose of an immunotherapeutically effective amount of an anti-inflammatory protein having a molecular weight of approximately 30–40 kD, depending on the extent of glycosylation, having amino acid sequence homology with the myxoma T7 interferon-γ receptor homolog, and having the biological function of the myxoma T7 interferon- The invention provides any pharmaceutical preparations and compositions containing the CBP-I of the invention for use in the method of the invention. The form will vary depending upon the route of administration. For example, compositions for injection can be provided in the form of an ampule, each containing a unit dose amount, or in the form of a container containing multiple doses.

CBP-I can be formulated into the therapeutic composition as neutralized pharmaceutically acceptable salt forms. These include the acid addition salts which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by selecting appropriate macromolecules, for example, polyesters, polyamino acids, polyvinyl pyrrolidone, ethylenevinylacetate, methylcellulose, carboxymethylcellulose, protamine sulfate, or lactide/glycolide copolymers. The rate of release of the CBP-I may be controlled by altering the concentration of the macromolecule.

Another method for controlling the duration of action comprises incorporating the CBP-I into particles of a polymeric substance such as polyesters, polyamino acids, hydrogels, polylactide/glycolide copolymers, or ethylenevinylacetate copolymers. Alternatively, it is possible to entrap CBP-I in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, beads, and lipid-based systems including oil-in-water emulsions, micelles, mixed micelles, and liposomes.

The following examples are intended to illustrate but not limit the invention. While they are typical of those that might be used, other procedures known to those skilled in the art may alternatively be used.

EXAMPLE 1

Materials and Methods
Rat model of injury induced atherosclerosis:
Nine Sprague Dawley rats had balloon angioplasty mediated injury of the left iliofemoral artery. A 1.5 mm USCI angioplasty balloon was advanced retrograde into the artery via cut down and arteriotomy under general pentobarbitol anesthetic (6.5 mg per 10 g weight by i.m. injection, Somnotrol, MTC Pharmaceuticals, Cambridge , Ontario). 500 pg of CBP-I (6 rats) or saline (5 rats) was given by intra-arterial injection of the CBP-I or control solution into the distal lumen of the angioplasty balloon catheter upstream from the site of subsequent balloon mediated damage. The balloon was then inflated to 8 bars pressure for 1.0 minutes. After angioplasty the balloon was deflated and with drawn and the arteriotomy site closed with local application of n-butyl cyanoacrylate monomer (Nexaband, Veterinary Products Laboratories, Phoenix, Ariz.). Each rat was maintained on a normal rat diet and was followed up for 4 weeks post surgery. At follow up the rats were sacrificed with 2.0 ml euthanyl per kg and the aorta was harvested for histological examination.

Rabbit model of injury induced atherosclerosis:
Seven cholesterol fed New Zealand white rabbits had balloon angioplasty of the distal abdominal aorta. All rabbits (strain New Zealand white) were fed 2% cholesterol in 10% peanut oil diet for 4 days/week, beginning 2 weeks before balloon injury. A 3–3.5 mm angioplasty balloon catheter ($\geq 1:1$ ratio of balloon to aorta diameter) was introduced via femoral arterial cut down following anesthetic (40 mg/kg ketalean, 8 mg/kg xylazene, and 0.5 mg/kg acepromazine by intramuscular injection). The balloon was inflated to 8 bars pressure in the distal abdominal aorta and advanced retrograde to the distal thoracic aorta. The balloon was advanced and withdrawn 3 times under flouroscopic control in each rabbit to ensure endothelial denudation. Contrast angiograms were recorded prior to and after balloon angioplasty mediated trauma and at 4 weeks follow-up. Heparin (400 units) was given immediately after obtaining femoral access to decrease catheter associated thrombosis.

Purified CBP-I (T7) protein, 500 pg per sample, was infused immediately after balloon mediated injury in the distal abdominal aorta of 4 rabbits. A parallel infusion of saline was infused locally into the distal abdominal aorta in 3 rabbits. Each infusate was administered via Wolinsky catheter in a total volume 10 ml diluted in sterile 0.9% saline immediately following balloon mediated injury. All infusions were via a 3.25 mm Wolinsky balloon (inflated to a final pressure of 6±1 bars for 2 minuets) in the abdominal aorta proximal to the iliac bifurcation. The Wolinsky balloon was positioned immediately above the iliac bifurcation under flouroscopic control such that the perfusion balloon was routinely located from 0.5–2.5 cm above the bifurcation and designated as the primary infusion site. Upstream secondary sites were defined in the region above 2.5 cm proximal to the iliac bifurcation. In all experiments, infusates were administered via Wolinsky catheter in a total volume of 10 ml diluted in sterile 0.9% saline immediately following balloon mediated injury. All infusions were via a 3.25 mm Wolinsky balloon (inflated to a final pressure of 6±1 bars for 2 minutes) in the abdominal aorta proximal to the iliac bifurcation.

CBP-I Protein isolation and purification:
Myxoma T-7 protein (CBP-I) was isolated and purified as described in EXAMPLE 4 herein.

Histology and morphometric analysis:
Histological analysis was performed at the primary site of Wolinsky infusion in the distal abdominal aorta (rabbits) or upper iliofemoral arterial branches (rat) representing the primary infusion site as defined by the original positioning of the perfusion balloon. In rabbits, internal control sections were taken from a downstream, non-infused site near the iliac bifurcation (0.5 cm above the bifurcation to 0.5 cm below the bifurcation). and in upstream, non-infused site (the upper abdominal aorta, 2.5 cm–3.5 cm above the iliac bifurcation). The area from 1.5–2.5 cm above the iliac bifurcation was considered a border zone with potentially variable infusion doses due to balloon placement and was therefore not included in this analysis. In rats the primary balloon sites for both T-7 treated and saline infused rats were used for histological assessment Hematoxylin and eosin staining of formalin fixed specimens was performed as previously described. Briefly, each specimen was fixed in 10% (v/v) sodium phosphate buffered formalin, processed, impregnated, embedded in paraffin and cut into 5 $\mu$m sections by microtome as has been previously described. Sections from each specimen (a minimum of 2 sections per site) were then stained with hematoxylin and eosin and examined by light microscopy.

Schwartzman reaction:

New Zealand White female rabbits weighing 3 kg are injected with lipopolysaccharide (LPS) of the E. coli serotype 0111:B4 (Sigma) and CBP-I (T7) protein which had been purified to homogeneity using column chromatography.

Eight intradermal injections (0.1 ml each) of 50–100 μg LPS in the presence and absence of 0.1–1.0 μg CBP-I was applied to the back of the rabbit; there are 4 injection sites on each side, separated by about 2.5 cm. 24h later 100 μg of LPS is administered to the rabbit intravenously in the marginal ear vein. About 4–6 h after the intravenous injection necrotic inflammation developed at the sites of intradermal injection. As soon as the inflammation was significant, the rabbit was sacrificed by a lethal injection of euthanol. The size and redness of the lesions are assessed, and tissue samples were collected.

EXAMPLE 2

Binding of Cytokines to a Novel Viral Protein

Briefly, a variety of human cytokines were radiolabelled with $^{125}$I, exposed to the secreted proteins harvested from control or poxvirus-infected BGMK cells, cross-inked, and then analyzed by SDS-PAGE for novel cytokine/protein complexes.

Surprisingly, cross-linking assay uncovered what was clearly a novel viral-specific protein that bound to each of the three human chemokines that was tested: IL-8, RANTES and MIP-1$\beta$ (FIG. 1). FIG. 1A shows gel mobility shift assays using iodinated ligands and tissue culture supernatants. Tissue culture supernatants (Sups) were prepared as follows: BGMK (Baby Green Monkey Kidney Cells) were infected with Myxoma (MYX), vaccinia virus (VV), or Shope fibroma virus (SFV) at a multiplicity of infection (MOI) of 3. To collect early Sups the infected monolayer was washed three times with phosphate buffered saline (PBS) and replenished with serum free medium which was then collected 4 h post infection (E). Late Sups were prepared by washing the monolayer three times with PBS and replenishing it with serum free medium at 4 h post infection; these Sups were then collected at 18 h post infection (L). Mock Sups were prepared in the same way in the absence of virus. Sups were concentrated approximately 15 fold using Amicon concentrators. The human chemokines IL-8, RANTES, and MIP- 1$\beta$ were labeled with $^{125}$I using iodobeads (Pierce) according to the manufacturer's protocols.

The gel mobility shift assays were performed as follows: 5 $\mu$l of iodinated ligand was mixed with 10 $\mu$l SUP and allowed to sit at room temperature for 2 hours. then 2 $\mu$l of the chemical cross linking reagent 1-ethyl-3-(3-dimethylaminopropyl)-carbodiimide (EDC) (200 mM in 100 mM potassium phosphate, pH 7.5) was added for 15 minutes, followed by an additional 2 $\mu$l for 15 minutes. The reaction was then quenched by the addition of 2 $\mu$l of Tris-HCl (1.0M, pH 7.5). The resulting mixture was analyzed using SDS-PAGE and autoradiography. The arrows indicate the shifted complexes.

FIG. 1B shows an experiment as described in FIG. 1A, however, iodinated MIP-1$\beta$ was reacted with mock, MYX or ectromelia (ECT) Sups.

The data show that cells infected with Shope fibroma virus (SFV) or myxoma (MYX) secreted a novel protein that created a cross-linked species (marked with arrow) of approximately 50 kD, indicating that the unknown species which bound to the 12 kD ligands was about 38 kD. Importantly, the novel complex was not detected in supernatants from control cells that were mock infected or cells that had been infected with vaccinia virus (VV), a poxvirus from a different genus (-orthopoxvirus) from that of SFV or myxoma (leporipoxvirus).

FIG. 2 shows gel mobility shift assays using $^{125}$I RANTES with competitors. Iodinated RANTES was mixed with 0, 1, 10, and 100 fold molar excess of unlabelled human RANTES, MIP-1$\beta$, MIP-1$\alpha$, IL-8, or MCAF. This mixture was then reacted with mock or myxoma early Sups as described in FIG. 1A and analyzed using SDS-PAGE and autoradiography. The figure shows self competition with RANTES as well as cross competition with MIP-1$\beta$, MIP-1$\alpha$, IL-8, and MCAF. The arrows indicate the shifted complexes.

In FIG. 3A, iodinated MIP-1$\beta$ was mixed with 0, 1, 10, and 100 fold molar excess of unlabelled human MIP-1$\beta$, IFN$\gamma$, MCAF, MIP-1$\alpha$, RANTES or IL-8. This mixture was then reacted with mock or myxoma early Sups as described in FIG. 1A and analyzed using SDS-PAGE and autoradiography. The figure shows self competition with MIP- 1$\beta$ as well as cross competition with IFN$\gamma$, MCAF, MIP-1$\alpha$, RANTES and IL-8. The arrows indicate the shifted complexes.

In FIG. 3B, iodinated MIP-1$\beta$ was mixed with Sups from mock, MYX, Cow Pox Virus (CPV), rabbit Pox Virus (RPV) ECT, SFV, or VV using SDS-PAGE and autoradiography. The arrows indicate the shifted complexes and the free ligand.

In FIG. 4, iodinated IL-8 was mixed with 0, 1, 10, and 100 fold molar excess of unlabeled human MIP-1$\beta$, MIP-1$\alpha$, MCAF, or IFN$\gamma$. This mixture was then reacted with mock or myxoma early Sups as described in FIG. 1A and analyzed using SDS-PAGE and autoradiography. The figure shows self competition with IL-8 as well as cross competition with MIP-1$\alpha$, MCAF, and IFN$\gamma$. The arrows indicate the shifted complexes.

As shown in FIG. 2, using $^{125}$I-labelled RANTES as a ligand, binding was able to be competed with a variety of cold chemokine competitors, including RANTES, MIP-1$\beta$, MIP-1$\alpha$ and MCP-1, but not IL-8. Similarly, using $^{125}$I-MIP-1$\beta$ as the labelled ligand, competition was observed with unlabelled MIP-1$\beta$, MCAF, MIP-1$\alpha$ and RANTES, but not IL-8 or human IFN-$\gamma$ (FIG. 3). However, when labelled IL-8 was used as the ligand, competition was observed with cold IL-8 as well as MIP-1$\alpha$, MIP-1$\beta$, MCAF but not IFN-$\gamma$ (FIG. 4).

It is interesting that the C-X-C and C-C chemokines have this curious pattern of cross-competitions, but it is possible that it relates to the various affinity constants of these different human chemokines with the viral protein. The apparent wide spectrum of chemokine binding to a viral 38 kDa secreted protein species suggested that this protein might be a generalized inhibitor of many human chemokines, and thus prevent chemotaxis of a wide variety of leukocytes.

In FIG. 5, T7 protein (CBP-I) was purified (see Example 3), mixed with the indicated cytokines, cross-linked and anlyzed by SDS-PAGE, followed by Western blotting with anti-T7 antibody. Of the cytokines tested, only human IL-8 and rabbit IFN-$\gamma$ formed high molecular weight complexes with T7, indicating the specificity of the binding.

In FIG. 6, a spectrum of representative chemokines from all three major classes (CXC, CC and C) were tested for binding to T7 protein (CBP-I), as described in FIG. 5. All chemokines tested bound T7 protein with comparable avidity.

EXAMPLE 3

Purification of CBP-I

Figure 7:
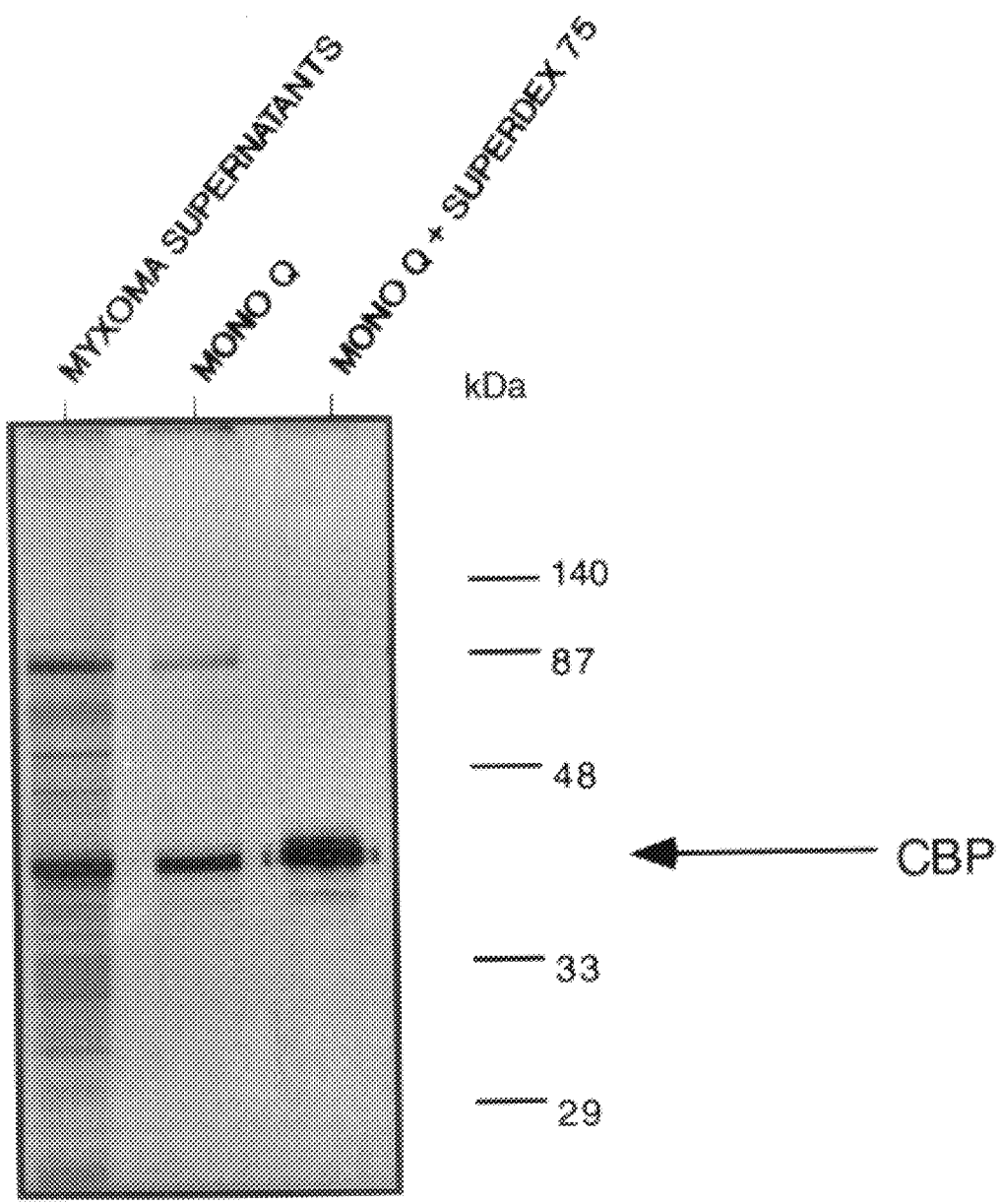
FIG. 7 shows an SDS-PAGE of total proteins from myxoma infected BGMK cells, semi-purified proteins after mono Q fractionation, and purified CBP-I (T7) protein after superdex 75 gel filtration.

To purify CBP-I, secreted proteins from myxoma infected cells were concentrated, fractionated by MonoQ chromatography and then size filtration chromatography. FIG. 7 shows the purification of CBP-I to homogeneity from supernatants of Myxoma virus infected cells. Briefly, supernatants from overnight myxoma virus infected Baby Green Monkey Kidney (BGMK) cells were harvested, centrifuged at 10,000 RPM for 1 hour, and concentrated 10-fold using a stirred Ultrafiltration Cell (Amicon). Virus-free concentrated myxoma supernatants (Sups) were dialysed in 20 mM bis-Tris pH 6.0 (Sigma) and stored at 4° C. prior to purification (Lane 1). CBP-I was purified to homogeneity from myxoma supernatants by a 2-step purification procedure using Fast Protein Liquid Chromatography (FPLC). Briefly, 5 mls of myxoma supernatants were loaded onto a MonoQ HR 5/5 (Pharmacia) anion exchange column pre-equilibriated with low ionic strength start buffer (20 mM bis-Tris pH 6.0). Proteins were eluted off the column by increasing the eluting buffer (1M NaCl 20 mM bis-Tris pH 6.0) to 500 mM NaCl in a step-gradient. Protein fractions were collected, resolved by SDS-PAGE, and analyzed by silver staining. Analysis of proteins that were eluted between 150–200 mM NaCl (fractions 21–27) revealed a prominent band of approximately 37,000 MW (CBP-I) and an unknown contaminating protein equivalent to the size of bovine serum albumin (Lane 2). Pooled MonoQ Fractions #21–27 were subsequently loaded onto a HiLoad 16/60 Superdex 75 gel filtration column (Pharmacia) and eluted at a flow rate of 0.5 ml/min using 20 mM bis-Tris pH 6.0. Fractions from the equivalent of 2 column bed volumes were collected, resolved by SDS-PAGE and analyzed by silver staining. Fractions #26–31 collected from the Superdex 75 flow-through volume, revealed a single protein species of approximately 37 kD corresponding to purified CBP-I (Lane 3).

The final CBP-I product (FIG. 7) was a 38 kDa glycosylated protein that co-purified with a smaller component (35 kDa) which appeared to be an under-glycosylated variant of CBP-I.

1 μg of purified or partially purified CBP-I was incubated with or without 1μ recombinant human RANTES for 2 hours at room temperature (RT). After incubation, the proteins were cross-linked by the addition of EDC (Sigma) to 40 mM (final concentration) at room temperature for 30 minutes and quenched by the addition of one-tenth volume 1M Tris (pH7.5). SDS-loading buffer was added to the mixtures, the samples were boiled for 30 minutes, subjected to SDS-PAGE, and detected by silver straining. Silver stain analysis revealed a cross-linked complex (CBP-I+RANTES) of approximately 47 kD when either purified or partially purified CBP-I was incubated with RANTES (Lanes 2 and 4), however no gel mobility shifted complex was observed in the absence of Rantes (Lanes 1 and 3).

Figure 8:
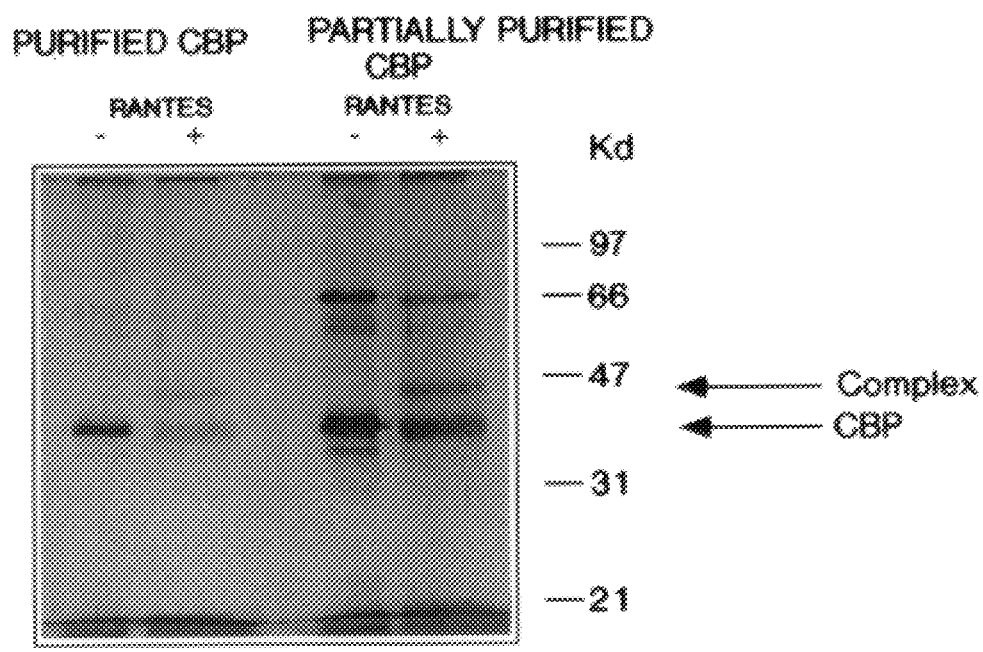
FIG. 8 shows binding of human RANTES chemokine to purified/partially-purified CBP-I. Silver stain analysis shows a cross-linked complex (CBP-I+Rantes) of approximately 47 kD when either purified or partially purified CBP-I was incubated with RANTES (Lanes 2 and 4); no gel mobility shifted complex was observed in the absence of RANTES (Lanes 1 and 3).
Figure 9:
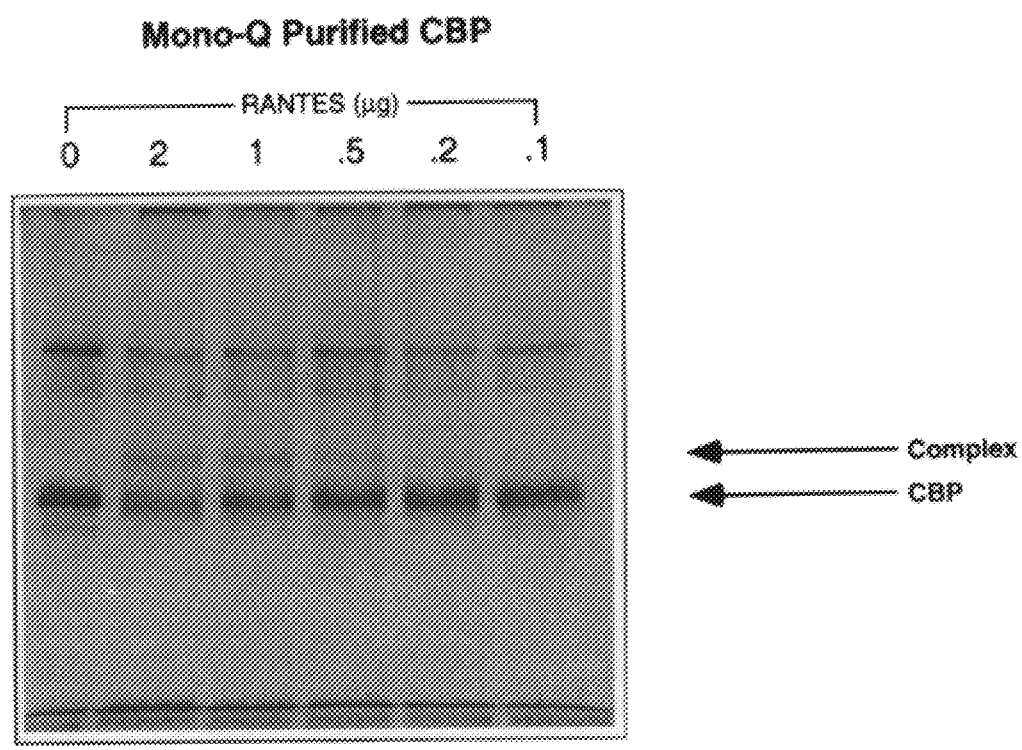
FIG. 9 shows the binding of human RANTES chemokine to partially-purified CBP-I. Silver stain analysis revealed a cross-linked binding complex (CBP-I+Rantes) of approximately 47 kD when CBP-I is incubated with biotinylated Rantes (Lanes 2–6), and this binding can be titrated out by decreasing amounts of the unlabelled chemokine ligand.

When the partially purified (i.e., MonoQ alone) or fully purified CBP-I were tested in standard cross lining assays with human RANTES, the appropriate shifted 1:1 complex of CBP-I/chemokines was detected, as predicted if the binding activity was a property conferred by CBP-1 alone (FIG. 8 and 9). FIG. 9 shows binding of human Rantes Chemokine to partially-purified CBP-I. 1 μg of partially purified CBP-I was incubated without (Lane 1) or with increasing amounts (Lane 2–6) of recombinant human Rantes for 2 hours at room temperature. After incubation, the proteins were cross-linked by the addition of EDC (Sigma) to 40 mM (final concentration) at RT for 30 minutes and quenched by the addition of one-tenth volume 1M tris (ph 7.5). SDS-loading buffer was added to the mixtures, the samples were boiled for 3 minutes, subjected to SDS-PAGE, and detected by silver staining. Silver stain analysis revealed a cross-linked binding complex (CBP-I+Rantes) of approximately 47 kD when CBP-I is incubated with Rantes (Lanes 2–6), and this binding can be titrated out by decreasing amounts of the chemokine ligand. A single contaminating band of approximately 66 kD that appears is an unknown protein that co-fractionates with CBP-I during MonoQ chromatography, but which is removed by Superdex 75 chromatography.

EXAMPLE 4

Analysis of the Efficacy of CBP-I (T-7) as an Anti-Restenosis Protein as Shown in Angioplasty Balloon Mediated Injury in Rat Remoral Arteries Inflammation has been associated with accelerated atherosclerotic plaque development in the arterial wall. There is a high rate of plaque recurrence, restenosis, after the use of balloon angioplasty and other related angioplasty devices designed to open occluded arteries. Accelerated atherosclerotic plaque growth also has been reported under conditions leading to arterial injury, viral infections, vasculitis, homocystinuria, diabetes melitis, hypertension, hyperlipideuria, smoking and immune complex generated disorders. The larger DNA viruses have evolved mechanisms, anti-inflammatory proteins, that allow the virus to proliferate in the host with decreased inhibition by the host immune and inflammatory defense mechanisms. These examples demonstrate the use of viral proteins as potential anti-inflammatory agents for the treatment of or prevention of immune based disorders. CBP-I (T-7) was tested as a potential therapeutic agent for the prevention of plaque growth after angioplasty. CBP-I has been reported to act as an interferon gamma receptor homologue and as a chemokine inhibitor. CBP-I was tested in 2 animal models of injury induced atherosclerosis (rat and rabbit) and the results show a significant decrease in plaque formation 4 weeks after infusion.

Figure 10A:
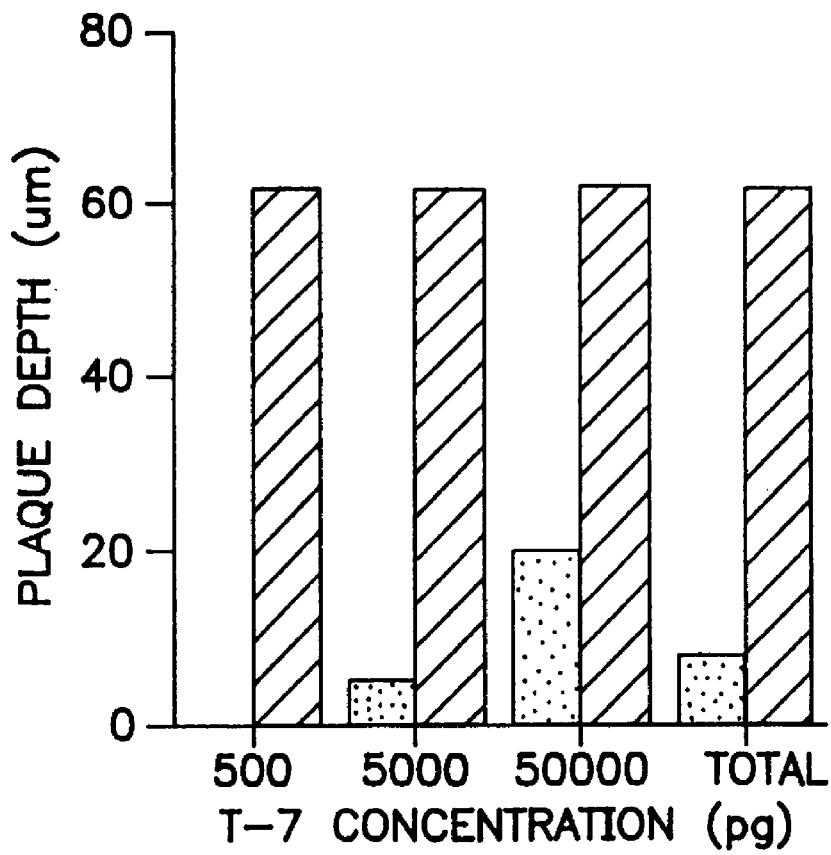
FIG. 10A shows plaque thickness/depth (mm) of atherosclerotic plaque in an arterial injury rat model 1 month after CBP-I (T7) treatment.
Figure 10B:
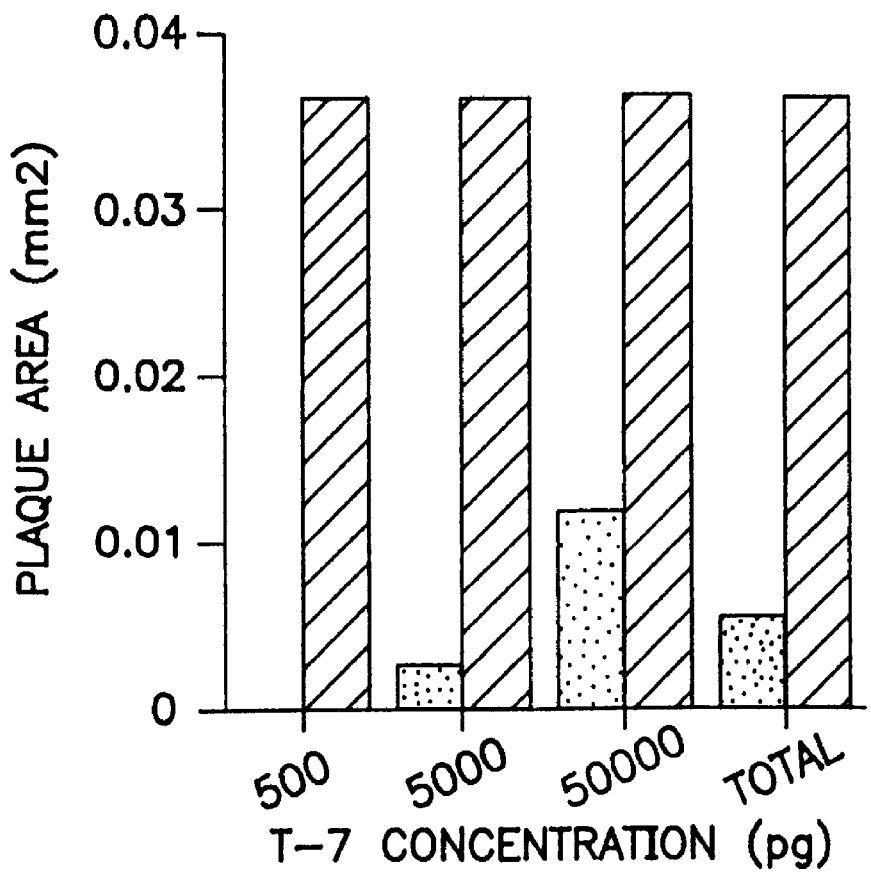
FIG. 10B and 10C show plaque area (mm2) of atherosclerotic plaque in an arterial injury rat model 1 month after CBP-I (T7) treatment.
Figure 10C:
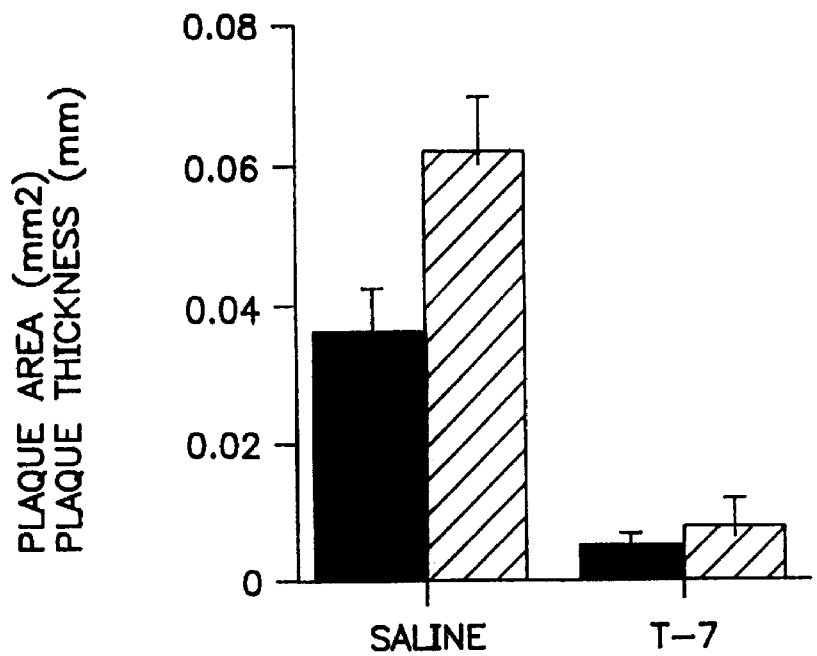

There was a significant decrease in plaque growth after CBP-I infusion on comparison with saline infusion. (FIG. 10A–C) In the rat model there was a mean plaque area of $0.005 \pm 0.002$ mm$^2$ (FIG. 10B, C) and a mean plaque thickness of $8.33 \pm 4.01$ μm (FIG. 10A) at 4 weeks follow up after CBP-I infusion (p(0.0003). With saline infusion the plaque area was $0.036 \pm 0.006$ mm$^2$ and the plaque thickness was $62 \pm 7.35$ μm at 4 weeks follow up (p(0.0001). this represents a 7 fold decrease in plaque area and in plaque thickness with CBP-I infusion. The decrease in plaque development was seen at 4 weeks follow up after only a single infusion of CBP-I immediately prior to balloon mediated injury. The visible lesions consisted predominately of smooth muscle cellular proliferative changes characteristic of the rat arterial injury model (FIG. 10).

Figure 11:
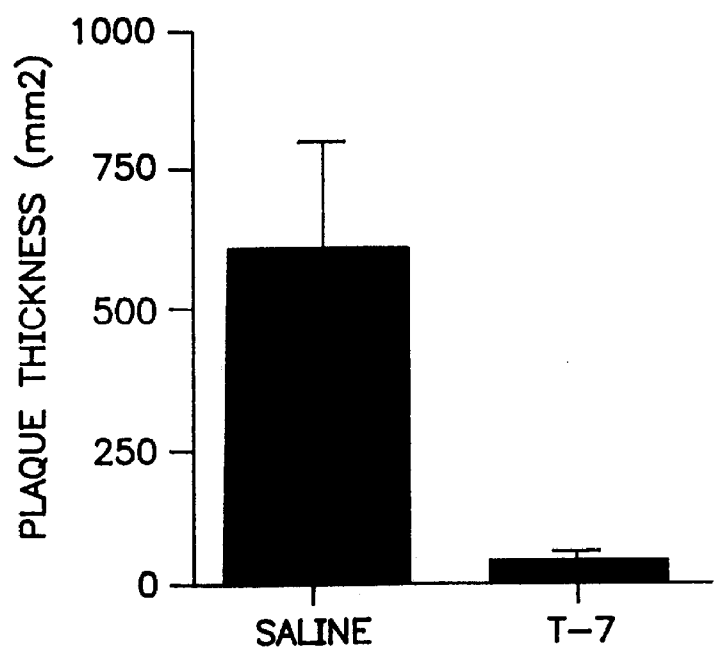
FIG. 11 shows plaque thickness (mm2) of atherosclerotic plaque in an arterial injury rabbit model 1 month after CBP-I (T7) treatment.

In the rabbit model there was also a significant decrease in plaque area and thickness on comparison with the saline treated controls. At 4 weeks follow up there was a mean plaque thickness of $30 \pm 21.6$ μm after CBP-I infusion and $600 \pm 200$ μm after saline infusion (p(0.02). In this case the plaque observed was the fibrous and fatty foam cell plaque commonly seen in the cholesterol fed rabbit models (FIG. 11).

Examination of the use of a viral anti-inflammatory protein in 2 models of injury induced atherosclerosis (rabbit and rat). In both models a significant decrease in subsequent plaque formation was detectable on histological analysis. In each case only a single infusion of the protein was given immediately following balloon injury.

EXAMPLE 5

Schwartzman Reaction

One of the classic examples of necrotizing inflammation is the Schwartzman reaction, in which lipopolysaccharide (LPS) is introduced first into rabbit skin and then, 24 hours later, followed by a second intravenous dose of the same LPS. Within hours after the second LPS injection, infiltrating macrophages induce a reproducible necrotizing response at the site of the primary injection which is highly reproducible and readily quantified. The ability of CBP-I to inhibit macrophage influx and activation at the primary injection site was examined.

LPS was injected intradermally on the back of a rabbit in the presence or absence of purified T7 protein and 24 h later an intravenous injection of LPS was administered. Inflammation quickly appears at the sites of intradermal injection, and the animals were euthanized and data was collected.

TABLE 1

Schwartzman Reaction in Rabbits

| LPS (µg) (intradermal) | lesion | LPS plus CBP-I (T7) (µg) (intradermal) | lesion |
|---|---|---|---|
| 100 | ++++ | 100 (LPS) + 1 (T7) | + |
| 50 | +++ | 50 (LPS) + 1 (T7) | − |
| 100 | ++++ | 100 (LPS) + 0.5 (T7) | ++ |
| 100 | ++++ | 100 (LPS) + 0.1 (T7) | +++ |

− = No reaction
+ to ++++ indicates the degree of inflammation from minimal to extreme The lesions were graded as follows: 1–10 mm in diameter, slightly red, not raised (+); 1–10 mm min diameter, red, raised 1–2 mm (++); 10–15 mm in diameter, intensley red, 2–3 mm raised (+++); more than 15 mm in diameter, intensley red with a dark haemoragic center, 2–3 mm raised (++++).

The LPS (100 µg) lesions were haemorrhagic and swollen, whereas skin injected with LPS (100 µg) plus CBP-I (T7) protein (1 µg) was slightly red and raised. When a dose of 50 µg of LPS was used 1 µg of CBP-I completely inhibited all visible signs of the Schwartzman reaction. CBP-I alone injected intradermally, followed by the intravenous LPS injection, induced no inflammation. Bovine serum albumin (1.0 µg) injected with 100 µg LPS, followed by the intravenous LPS injection, was not able to inhibit inflammation. These experiments (n=2) demonstrate that purified CBP-I protein was able to protect the rabbit from the localized Schwartzman reaction.

As T7 has been shown to bind both IFNγ and chemokines such as IL8 and RANTES, the involvement of these cytokines in the Schwartzman reaction is of interest. The Schwartzman reaction is complex involving the cytokines IL-12, IFNγ, TNFα(Ozmen et al., *J. Exp. Med.*, 180:907–915, 1994.) and IL8 (Harada, et al., *Int. Immunol.*, 5:681–690, 1993). For example, it has been shown that neutralizing antibodies to either IFNγ(Billiau et al., *Euro. J Immunol*, 17:1851–1854, 1987; Heremans, *J. Immunol.*, 138:4175–4179, 1987) or IL8 (Harada et al., supra.) block or inhibit the Schwartzman reaction. Thus, the inhibitory effect of CBP-I on the Schwartzman reaction in rabbits could be due to it ability to bind IFNγ, or chemokines, or both. As CBP-1 shows species specificity for IFNγ but not chemokine binding, these experiments will be repeated in rats in the attempt to distinguish between the IFNγ and chemokine binding activity of T7 in this model of inflammation.

SUMMARY

The cloned and sequenced myxoma CBP-I gene, which is not a secreted homologue of the known chemokine receptors, which all possess seven membrane-spanning domains (and are called "serpentines") and are described in numerous recent reviews (Kelvin, D. J., et al., *J. Leukocyte Biol.*, 54:604–612, 1993; Murphy, P. M., *Ann. Rev. Imm.*, 12:593–633, 1994; Horuk, R., *Imm. Today.*, 15:169–174, 1994; and Horuk, R., *Trends in Pharm. Sci.*, 15:159–165, 1994). Although some DNA viruses do encode homologues of such serpentine receptors (Ahuja, S. K., et al., *Imm. Today*, 15:281–287, 1994), including at least one gene candidate in a poxvirus (Massung, R. F., et al., *Virology*, 197:511–528, 1994), the CBP-I of the present invention is not a member of this particular receptor family. Thus, CBP-I represents a new class of anti-inflammatory protein that acts by presumably modulating a spectrum of chemokines in treated tissues.

Although the invention has been described with reference to the presently preferred embodiment, it should be understood that various modifications can be made without departing from the spirit of the invention. Accordingly, the invention is limited only by the following claims.

We claim:

1. A method for treating a chemokine related immunopathological disorder having an etiology associated with an influx of leukocytes, wherein the chemokine is a class α or a class β chemokine, in a subject comprising administering to the subject a therapeutically effective amount of a chemokine binding protein having an amino acid sequence as set forth in SEQ ID NO: 2.

2. The method of claim 1, wherein the chemokine is selected from the group consistng of CTAP-III, gro/MGSA, ENA-78, MCP-1, interleukin-8, RANTES, MIP-1α, MIP-1η, PF-4, IP-10, and NAP-2.

3. The method of claim 1, wherein the immunopathological disorder is selected from the group consisting of microbial infection, malignancy and metastasis, asthma, coronary restenosis, autoimmune diseases, cirrhosis, endotoxemia, atherosclerosis, and reperfusion injury.

4. The method of claim 1, further including administering an antibiotic or antiviral to the subject.

5. The method of claim 1, wherein the administering of anti-inflammatory protein is at a dosage from about 10 pg to 100 µg per administration.

6. The method of claim 1, wherein the administering of anti-inflammatory protein is selected from the group consisting of subcutaneous, intravenous, intraarterial, intramuscular, intrarectal and transdermal.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1877 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:

(B) CLONE: CBP (ix) FEATURE:
(A) NAME/KEY: CDS
(B) LOCATION: 455..1243

(xi) SEQUENCE DESCRIPTION: SEQ ID NO:1:

```
GGATCCATCG AGACGGCGTC CCGGACGTCA CGGACTTCGT TCAGAAACTA TCCGGAGGTA      60

CATGGACGAA GGTGAACGAA CTGTCCGTCC CCAAGGCGAG CGTTACGGCG ATCGTCTATA     120

AAGAGAGGTT GTACTGCGTA GGGGGGCTGG TGGATCGATA CGCTCCAACG AACGAAGTTA     180

TCCGTTACAG GGACGACACG AACGAGTGGG AATACGTGGG ATCTACGAAG ATCGAACGAG     240

GCGGTTCCGT GGGGTGTGTG TACAACGACG AGCTCTACGT CTTCGGAGGA ACGGATACGT     300

TTACGTCCGA GCGATACAAC GGAGTCATTT GGAAACGAGC GAACGACGTC TCCTGTCACT     360

TCGCCACCAT GAACGCGGCG TACGCCACCT ACCTCGAGCT GTAGAAACGT TTTTATAACT     420

GAAAAAGTAT CCTAAAAATA GAGTAATACT CAAG ATG GAC GGG AGA CTG GTG         472
                                     Met Asp Gly Arg Leu Val
                                      1               5

TTT CTC CTC GCG TCG CTC GCT ATC GTC TCC GAC GCC GTA CGC CTT ACG       520
Phe Leu Leu Ala Ser Leu Ala Ile Val Ser Asp Ala Val Arg Leu Thr
         10                  15                  20

TCC TAC GAC TTA AAC ACA TTC GTT ACG TGG CAA GAC GAT GGA TAC ACC       568
Ser Tyr Asp Leu Asn Thr Phe Val Thr Trp Gln Asp Asp Gly Tyr Thr
     25                  30                  35

TAC AAC GTC AGT ATT AAA CCG TAT ACG ACG GCT ACG TGG ATC AAT GTG       616
Tyr Asn Val Ser Ile Lys Pro Tyr Thr Thr Ala Thr Trp Ile Asn Val
 40                  45                  50

TGT GAA TGG GCG TCT TCT AGC TGC AAC GTA TCT CTC GCC CTA CAA TAC       664
Cys Glu Trp Ala Ser Ser Ser Cys Asn Val Ser Leu Ala Leu Gln Tyr
 55                  60                  65                  70

GAT TTG GAC GTC GTG TCT TGG GCC AGA CTG ACC CGG GTT GGT GGG TAC       712
Asp Leu Asp Val Val Ser Trp Ala Arg Leu Thr Arg Val Gly Gly Tyr
                 75                  80                  85

ACA GAA TAC AGT CTG GAA CCG ACG TGT GCC GTG GCT CGG TTC TCT CCA       760
Thr Glu Tyr Ser Leu Glu Pro Thr Cys Ala Val Ala Arg Phe Ser Pro
             90                  95                 100

CCG GAG GTA CAA CTC GTA AGA ACA GGT ACC AGC GTA GAA GTC TTA GTT       808
Pro Glu Val Gln Leu Val Arg Thr Gly Thr Ser Val Glu Val Leu Val
        105                 110                 115

AGA CAC CCC GTC GTG TAT CTA CGG GGG CAG GAA GTG TCC GTC TAC GGA       856
Arg His Pro Val Val Tyr Leu Arg Gly Gln Glu Val Ser Val Tyr Gly
    120                 125                 130

CAT TCA TTC TGC GAC TAC GAC TTC GGG TAT AAA ACG ATC TTC CTG TTC       904
His Ser Phe Cys Asp Tyr Asp Phe Gly Tyr Lys Thr Ile Phe Leu Phe
135                 140                 145                 150

TCG AAG AAT AAA CGA GCG GAG TAC GTC GTA CCC GGC CGA TAT TGC GAC       952
Ser Lys Asn Lys Arg Ala Glu Tyr Val Val Pro Gly Arg Tyr Cys Asp
                155                 160                 165

AAC GTA GAG TGT CGT TTC TCC ATC GAT TCC CAA GAA AGT GTA TGT GCT      1000
Asn Val Glu Cys Arg Phe Ser Ile Asp Ser Gln Glu Ser Val Cys Ala
            170                 175                 180

ACG GCG GTT CTT ACG TAC GGT GAC AGT TAT CGT TCC GAG GCG GGT GTG      1048
Thr Ala Val Leu Thr Tyr Gly Asp Ser Tyr Arg Ser Glu Ala Gly Val
        185                 190                 195

GAG GTC TGC GTT CCC GAA CTC GCG AAG AGA GAA GTC AGT CCC TAC ATC      1096
Glu Val Cys Val Pro Glu Leu Ala Lys Arg Glu Val Ser Pro Tyr Ile
    200                 205                 210

GTG AAA AAG TCG TCC GAC CTG GAA TAC GTC AAA CGT GCC ATA CAC AAC      1144
Val Lys Lys Ser Ser Asp Leu Glu Tyr Val Lys Arg Ala Ile His Asn
```

```
                 215                     220                     225                     230
GAA   TAC   CGA   CTC   GAC   ACC   TCC   TCC   GAG   GGA   CGC   AGA   TTG   GAG   GAA   CTG    1192
Glu   Tyr   Arg   Leu   Asp   Thr   Ser   Ser   Glu   Gly   Arg   Arg   Leu   Glu   Glu   Leu
                        235                     240                           245

TAT   CTA   ACG   GTC   GCC   TCC   ATG   TTT   GAA   CGT   CTC   GTG   GAA   GAT   GTC   TTC    1240
Tyr   Leu   Thr   Val   Ala   Ser   Met   Phe   Glu   Arg   Leu   Val   Glu   Asp   Val   Phe
                  250                           255                     260

GAA   TAATCGAAAT   ATAAATAATG   TAGTTTTTGT   ATCGGAATCA   TGGAACGTAC                             1293
Glu

CCTGGTAAGT   TTCTTGGACA   GCGGTACCAT   GAGCGACATC   ACCCTCGTCG   CGGGGGAGAC                      1353

GTCGTTCACG   GCGCATCGAC   TGATTTTATC   CGTCCATTCG   GATTACTTCT   ATCGTCTGTT                      1413

TAACGGAGT    TTTGAGGTAC   CGGATACGAT   CACGTTGGAT   ACGGACGATG   GCGTCCTTCG                      1473

CACCGTGCTC   CGCTACATGT   ACACGGGATA   CAGCAACATA   CGAGACCGTA   CCGTAGAGGA                      1533

TCTACAATCC   ATTATCGTAT   TGGCGGACTA   CCTGGGTATA   ACGAAACTGG   TGAAAGAGTG                      1593

TGCGGATTAC   ATGGTAAGTC   GAGTGGACCC   GACGAACTGC   GTATCCGCTT   CCAGTTTGC                       1653

AGAGACGTAT   CACATAGAGG   ATTTAAAACG   AAACCTCAAT   ACGTTCTTAC   CCGAACTCTT                      1713

GCTGAACTCC   CGAGGGGCGT   TTACGAAATT   GGATACGGAC   GAAGCGGTCG   TGGTTCTACG                      1773

AGCGTCCTAC   GAGATCGTCG   ACAGACGGTT   TGTGCTTAAG   GCTATTCTAG   ATTGGGTGCG                      1833

AAAAGGACCC   AAACGCATCG   AGCGGATAAA   GACGCTGTCC   GCGG                                         1877
```

( 2 ) INFORMATION FOR SEQ ID NO:2:

( i ) SEQUENCE CHARACTERISTICS:
      ( A ) LENGTH: 263 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met   Asp   Gly   Arg   Leu   Val   Phe   Leu   Leu   Ala   Ser   Leu   Ala   Ile   Val   Ser
 1                      5                       10                            15

Asp   Ala   Val   Arg   Leu   Thr   Ser   Tyr   Asp   Leu   Asn   Thr   Phe   Val   Thr   Trp
                  20                      25                            30

Gln   Asp   Asp   Gly   Tyr   Thr   Tyr   Asn   Val   Ser   Ile   Lys   Pro   Tyr   Thr   Thr
            35                      40                      45

Ala   Thr   Trp   Ile   Asn   Val   Cys   Glu   Trp   Ala   Ser   Ser   Cys   Asn   Val
      50                      55                      60

Ser   Leu   Ala   Leu   Gln   Tyr   Asp   Leu   Asp   Val   Val   Ser   Trp   Ala   Arg   Leu
 65                     70                      75                            80

Thr   Arg   Val   Gly   Gly   Tyr   Thr   Glu   Tyr   Ser   Leu   Glu   Pro   Thr   Cys   Ala
                        85                      90                      95

Val   Ala   Arg   Phe   Ser   Pro   Pro   Glu   Val   Gln   Leu   Val   Arg   Thr   Gly   Thr
                  100                     105                     110

Ser   Val   Glu   Val   Leu   Val   Arg   His   Pro   Val   Val   Tyr   Leu   Arg   Gly   Gln
            115                     120                     125

Glu   Val   Ser   Val   Tyr   Gly   His   Ser   Phe   Cys   Asp   Tyr   Asp   Phe   Gly   Tyr
      130                     135                     140

Lys   Thr   Ile   Phe   Leu   Phe   Ser   Lys   Asn   Lys   Arg   Ala   Glu   Tyr   Val   Val
145                           150                     155                           160

Pro   Gly   Arg   Tyr   Cys   Asp   Asn   Val   Glu   Cys   Arg   Phe   Ser   Ile   Asp   Ser
                        165                     170                     175

Gln   Glu   Ser   Val   Cys   Ala   Thr   Ala   Val   Leu   Thr   Tyr   Gly   Asp   Ser   Tyr
                  180                     185                     190
```

-continued

| Arg | Ser | Glu | Ala | Gly | Val | Glu | Val | Cys | Val | Pro | Glu | Leu | Ala | Lys | Arg |
|  |  | 195 |  |  |  |  | 200 |  |  |  |  | 205 |  |  |  |
| Glu | Val | Ser | Pro | Tyr | Ile | Val | Lys | Lys | Ser | Ser | Asp | Leu | Glu | Tyr | Val |
|  | 210 |  |  |  |  | 215 |  |  |  |  | 220 |  |  |  |  |
| Lys | Arg | Ala | Ile | His | Asn | Glu | Tyr | Arg | Leu | Asp | Thr | Ser | Ser | Glu | Gly |
| 225 |  |  |  |  | 230 |  |  |  |  | 235 |  |  |  |  | 240 |
| Arg | Arg | Leu | Glu | Glu | Leu | Tyr | Leu | Thr | Val | Ala | Ser | Met | Phe | Glu | Arg |
|  |  |  |  | 245 |  |  |  |  | 250 |  |  |  |  | 255 |  |
| Leu | Val | Glu | Asp | Val | Phe | Glu |
|  |  |  | 260 |  |  |  |